Nov. 25, 1969 D. L. ARMSTRONG Plant Pat. 2,943
NECTARINE TREE
Filed March 14, 1968
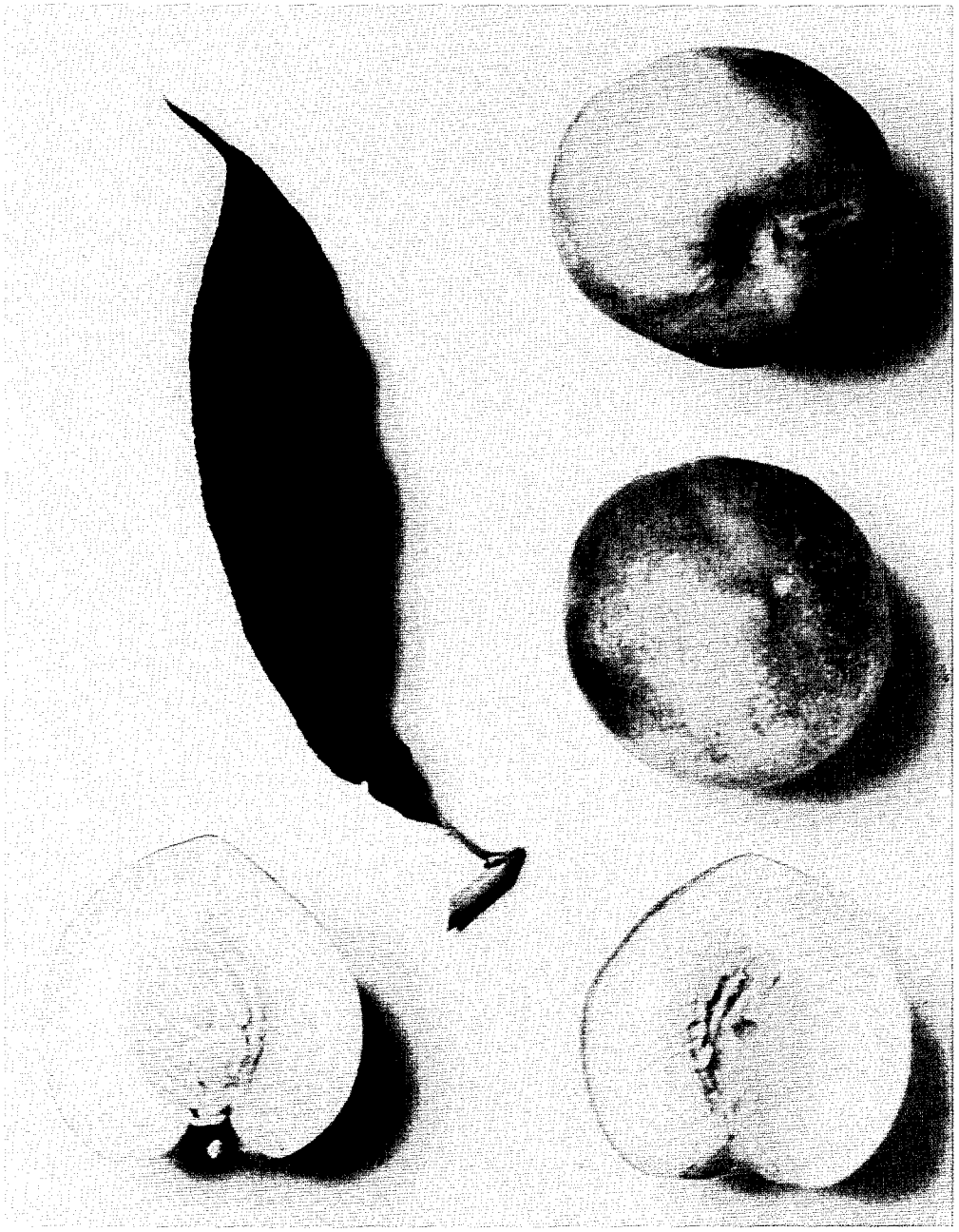
Inventor.
D. L. Armstrong
By: Robb & Robb
Attorneys.

United States Patent Office

Plant Pat. 2,943
Patented Nov. 25, 1969

2,943
NECTARINE TREE

David L. Armstrong, Ontario, Calif., assignor to Armstrong Nurseries, Inc., Ontario, Calif., a corporation of California Filed Mar. 14, 1968, Ser. No. 713,264
Int. Cl. A01h 5/08
U.S. Cl. Plt.—41 1 Claim The present invention relates to a new and distinct variety of nectarine tree of the yellow-fleshed fruit-bearing type, which was originated by me as a seedling resulting from crossing two unnamed and unpatented siblings derived from crossing the nectarine variety known as "Palomar" (Plant Patent No. 1,652) × the peach variety known as "Springtime" (Plant Patent No. 1,268).

The primary objective of this breeding was to produce an improved early-ripening, yellow-fleshed nectarine of commercial quality. This objective was fully achieved, along with other commercially desirable features, as evidenced by the following unique combination of characteristics which are outstanding in the new variety and which distinguish it from its parents, as well as from all other nectarine varieties of which I am aware:

(1) A vigorous tree habit, with a chilling requirement approximately that of "Springtime" peach (Plant Patent No. 1,268), or very slightly greater;
(2) The production of large crops of fruit of relatively large size and attractive appearance for fruit of such a ripening season as that of the new variety;
(3) A fruit ripening period which, on the average, is in the ripening season of "Robin" peach (Plant Patent No. 529) or very close to the average ripening season of "Armred" nectarine (Plant Patent No. 2,580);
(4) Uniform fruit size, with a rounded to truncate fruit shape;
(5) An attractive fruit color, with a contrast of Canary Yellow to Straw Yellow ground color, heavily overlaid on one side with a red coloration which becomes particularly bright at the tree-ripe stage;
(6) Smooth fruit skin which is characteristic of the nectarine, without pubescence;
(7) Yellow fruit flesh, with only a slight trace of red in the apical area when the fruit is tree-ripe;
(8) A tendency for the fruit flesh to cling to the stone to a slight degree until it is fully ripe, characteristic of early-ripening peaches and nectarines; and
(9) A distinctive and pleasing nectarine flavor, with a good balance between sugar and acid.

The unnamed seed parent of this new variety was a yellow-fleshed, freestone peach which bears fruit which ripens about the same time as "Redglobe" peach (unpatented) on the average, said fruit being large in size, nearly round in shape and having moderately good red skin color, and the tree is productive, with a medium chilling requirement approximately equal to that of "Robin" peach, but slightly greater on the average.

The unnamed pollen parent of the new variety was a yellow-fleshed, freestone peach which bears fruit which ripens on the average about four days after "June Gold" peach (Plant Patent No. 1,884), said fruit being from medium to large in size, with a fair to good red skin color.

In comparison with its seed parent, the new variety is distinguished therefrom primarily by being a nectarine instead of a peach, and its fruit ripens approximately six weeks earlier than the fruit of this parent.

As compared with its pollen parent, the new variety is distinguished therefrom by being a nectarine instead of a peach, and its fruit ripens on the average slightly over two weeks earlier than the fruit of this parent.

The new variety is distinguished from its grandparent, "Palomar" nectarine, by the somewhat smaller size of its fruit, but more importantly, by the much earlier ripening habit of the fruit of the new variety—nearly two months earlier.

The new variety is also distinguished from its ancestor, "Springtime" peach, by the fact that it is a nectarine and bears yellow-fleshed fruit, whereas the ancestor is a peach and bears white-fleshed fruit.

The new variety is distingushed from the nectarine variety believed to be closest to its in both appearance and ripening season, namely, the "Armred" nectarine, by the fact that the new variety ripens on the average from two to four days earlier and the fruit averages slightly larger in size, and owing to the firmness of the fruit, the latitude in picking is slightly greater, thereby permitting a somewhat greater development of the skin color of the fruit of the new variety.

Asexual reproduction of my new nectarine variety by budding, as performed by me at Wasco, Calif., shows that the foregoing characteristics and distinctions come true to form and are established and transmitted through succeeding propagations.

The accompanying drawing shows typical specimens of the foliage, stem, fruit and stone of my new variety, with both exterior and sectional views of the fruit being shown, and all of said views being depicted in color as nearly true as is reasonably possible to make the same in a color illustratiion of this character.

The following is a detailed description of my new variety, as based upon observations of specimens grown at Wasco, Calif., with color terminology in accordance with Robert F. Wilson's Horticultural Colour Chart (hereinafter abbreviated as W and Ridgway's Color Standards and Nomenclature (hereinafter abbreviated as R, except where general color terms of ordinary dictionary significance are obvious:

*Tree*

Habit: Vigorous; upright-spreading.
Chilling requirement: Moderate; from about equal to that of "Springtime" peach to very slightly greater, as observed at Wasco, Calif.
Fruit production: Heavy crop bearer.
Current growth:
*Surface texture.*—Smooth at first, with lenticels small and minute; with age, some larger, cracked, slightly raised lenticels appear toward the base of the more vigorous shoots.
*Color.*—Green at first, or reddish on exposed surfaces, with lenticels appearing as small, nearly white dots, all becoming more brown with age.
Two-year wood:
*Surface texture.*—Generally smooth, with slightly raised, irregular, longitudinal striations and numerous lenticels.
*Color.*—Brown.
Old wood:
*Surface texture.*—Generally smooth, with moderate number of large, raised lenticels, and some small, longitudinal fissures.
*Color.*—From grey to greyish-brown, or reddish-brown on more exposed surfaces.
Leaves:
*Size.*—Length—from 5½ inches to 7 inches. Width—from 1¼ inches to 1¾ inches.
*Shape.*—Lanceolate, with apex acuminate.
*Color (mature).*—Upper surface—Near Deep Dull Yellow-Green (1), Plate XXXII (R). Under surface—Near Chromium Green, Plate XXXII (R).
*Petiole.*—Medium length; from medium thickness to thick.

*Margin.*—Finely serrate; glandular.

*Glands.*—Mostly globose, but occasionally near reniform; medium size; usually 3 or 4, but sometimes 5 or 6 in number; borne both on the petiole and on the base of the blade.

Vegetative buds:

*Size.*—Small.

*Shape.*—Ovoid, unless compressed between flower buds.

*Scales.*—Thick pubescence; moderate length.

*Color.*—Dark brown.

*Flowers*

Dates of first and full bloom: Over a period of four years at Wasco, Calif., first bloom varied from February 23 to March 4, and full bloom varied from March 7 to March 14, but averages were about equal to the bloom time of "Springtime" peach.

Dormant flower buds:

*Shape.*—Ovoid.

*Scales.*—Pubescent.

*Color.*—Dark brown, with pubescence giving a whitish effect.

Size (open flower): Small; non-showy.

Petalage (open flower): Single; usually 5 petals.

Form (open flower): Cupped.

Color (open flower): Dark pink.

*Fruit*

Ripening dates: Generally ripens in late May to early June at Wasco, Calif.; over six years of observations, first ripening ranged from May 25 to June 10; ripens in the general period of a few days to one week after "Mayred" nectarine (Plant Patent No. 2,758), averaging 5 days later, about 10 days to two weeks after "Springtime" peach, averaging about 12 days later, and a few days ahead to about the same time as "Robin" peach.

Maturity when described: Hard-ripe.

Size: From medium to large for its season.

*Axial diameter.*—From 2¼ inches to 2½ inches.

*Transverse diameter in suture plane.*—From 2¼ inches to 2½ inches.

*Transverse diameter at right angles to suture plane.*—From 2¼ inches to 2½ inches.

Form: Relatively uniform; globose; sometimes slightly compressed laterally.

Suture: Generally shallow; extending from base to apex on ventral side; slight depression beyond pistil point.

Ventral surface: Rounded; usually lipped throughout; lips usually unequal.

Stem cavity: Usually rounded; sometimes slightly elongated in suture plane, with suture showing on one side.

*Depth.*—From ¼ inch to ⅜ inch.

*Width.*—From ¾ inch to 1 inch.

Base: From rounded to truncate.

Apex: Generally rounded; sometimes slight conical shape to end of fruit; pistil point insignificant.

Stem: From medium caliper to thick; glabrous; weak adherence to stone.

*Length.*—From about ¼ inch to ⅜ inch.

Skin:

*Thickness.*—From medium to thin.

*Texture.*—Medium.

*Tenacity to flesh.*—Free.

*Pubescene.*—None; characteristic smooth skin of the nectarine.

*Color.*—Ground color varies from near Canary Yellow, Plate 2/1, page 2 (W) to near Straw Yellow, Plate 604/1, page 67 (W), heavily flushed with from near Jasper Red, Plate 018/1, page 107 (W) to near Oxblood Red, Plate 00823/3, page 191 (W), with the red coloring often mostly on one side and the other side being speckled, with the lighter ground color showing through, and the red coloring becoming particularly bright and glossy in effect right at tree-ripe stage, and more so in some years than in others.

Flesh:

*Quality.*—Medium firm; melting; fine texture.

*Aroma.*—Pronounced.

*Flavor.*—Distinctive nectarine flavor, with good balance between sugar and acid.

*Color.*—Between Lemon Yellow, Plate 4/2, page 4 (W) and Buttercup Yellow, Plate 5/2, page 5 (W); surface of pit cavity between Canary Yellow, Plate 2/2, page 2 (W) and Aureolin, Plate 3/2, page 3 (W).

Stone:

*Tenacity of flesh.*—Basically free, but because of early ripening, stone adheres to flesh along both dorsal and ventral edges until the fruit is fully ripe, and to a slight extent on other surfaces.

*Size.*—From medium to large. Length—from about 1¼ inches to 1½ inches. Width—from about 1 inch to 1⅛ inches. Thickness—from about ¾ inch to ⅞ inch.

*Form.*—Ovoid.

*Base.*—Somewhat oblique.

*Hilum.*—Narrow and oblong.

*Apex.*—Acute.

*Sides.*—Only slightly unequal; curved on right and left sides; irregularly furrowed toward apex; pitted toward base.

*Ventral edge.*—Medium thickness; usually without wing toward base.

*Dorsal edge.*—Narrow; with shallow, narrow groove toward base; ridges on either side interrupted.

*Color.*—Between Vinaceous-Cinnamon, Plate XXIX (R) and Pinkish Cinnamon, Plate XXIX (R).

I claim:

1. A new and distinct variety of nectarine tree of the yellow-fleshed, fruit bearing type, substantially as herein shown and described, characterized particularly as to novelty by the unique combination of a vigorous tree habit, with a chilling requirement approximately that of "Springtime" peach (Plant Patent No. 1,268), or very slightly greater, the production of large crops of fruit of relatively large size and attractive appearance for fruit of such a ripening season as that of the new variety, a fruit ripening period which, on the average, is in the ripening season of "Robin" peach (Plant Patent No. 529) or very close to the average ripening season of "Armred" nectarine (Plant Patent No. 2,580), uniform fruit size, with a rounded to truncate fruit shape, an attractive fruit color, with a contrast of Canary Yellow to Straw Yellow ground color, heavily overlaid on one side with a red coloration which becomes particularly bright at the tree-ripe stage, smooth fruit skin which is characteristic of the nectarine, without pubescence, yellow fruit flesh, with only a slight trace of red in the apical area when the fruit is tree-ripe, a tendency for the fruit flesh to cling to the stone to a slight degree until it is fully ripe, characteristic of early-ripening peaches and nectarines, and a distinctive and pleasing nectarine flavor, with a good balance between sugar and acid.

No references cited.

ROBERT E. BAGWILL, Primary Examiner